United States Patent [19]

Dewar

[11] Patent Number: 4,628,922

[45] Date of Patent: Dec. 16, 1986

[54] FRACTURE REDUCTION APPARATUS

[75] Inventor: Michael E. Dewar, London, England

[73] Assignee: University College London, London, England

[21] Appl. No.: 781,244

[22] Filed: Sep. 27, 1985

[30] Foreign Application Priority Data

Sep. 28, 1984 [GB] United Kingdom ............. 8424579

[51] Int. Cl.$^4$ .............................................. A61F 5/04
[52] U.S. Cl. .............................. 128/92 Z; 128/92 ZW
[58] Field of Search ................ 128/92 R, 92 A, 84 B

[56] References Cited

U.S. PATENT DOCUMENTS

| | | | |
|---|---|---|---|
| 2,101,889 | 12/1937 | Anderson | 128/92 A |
| 2,333,033 | 10/1943 | Mraz | 128/92 A |
| 2,346,346 | 4/1944 | Anderson | 128/92 A |
| 4,535,763 | 8/1985 | Jaquet | 128/92 A |

FOREIGN PATENT DOCUMENTS

| | | | |
|---|---|---|---|
| 615923 | 6/1978 | U.S.S.R. | 128/92 A |
| 740241 | 6/1980 | U.S.S.R. | 128/92 A |
| 986405 | 1/1983 | U.S.S.R. | 128/92 A |

Primary Examiner—Robert Peshock
Assistant Examiner—C. W. Shedd
Attorney, Agent, or Firm—McAulay, Fields, Fisher, Goldstein & Nissen

[57] ABSTRACT

A fracture reduction apparatus comprises a first holder for holding first set of bone fixation pins, and a second holder for holding a second set of bone fixation pins, the first and second sets of bone fixation pins being located, in use, with the site of the fracture intermediate them. Each of the holders is rotatable about a respective set of three orthogonal axes, the three axes of each set intersecting one another at a respective point located in the bone, the two respective points being spaced from one another along the longitudinal axis of the bone.

6 Claims, 6 Drawing Figures

FRACTURE REDUCTION APPARATUS

FIELD AND BACKGROUND OF THE INVENTION

This invention relates to the field of orthopaedics, and in particular to an apparatus for use in external fixation.

A variety of techniques are known for holding together the parts of a fractured bone while healing is taking place. One such technique, which is most usually employed for fractures of the tibia, is external fixation. This involves passing a plurality of pins usually two or three, through each of the parts of the bone so that the pins emerge through the skin of the patient. The pins may either emerge from the skin on only one side of the bone (single-sided fixation) or they may emerge on both sides (double-sided fixation). In what follows, only single-sided fixation will be referred to, but it is to be understood that what is described applied with appropriate modifications also to double-sided fixation.

In most known forms the emerging ends of the pins are connected to a frame by adjustable clamps, and after the bone has been manipulated to reduce the fracture the clamps are tightened to hold the parts of the bone fixed with respect to one another and in the correct position. There are two main difficulties associated with this procedure. Firstly, accurate reduction of a fracture in three dimensions is very difficult and time consuming. Secondly, a frame which allows all the movements necessary for accurate reduction is of necessity complicated since a large number of lockable joints are necessary. Once reduction and fixation have been achieved a complicated and cumbersome apparatus remains attached to the patient. Systems have been designed which attempt to simplify the frame, but in these the relative movement of the pins is restricted and hence the accuracy of reduction possible is reduced.

U.K. Pat. No. 2095999 provides means by which the functions of fracture reduction and fixation can be separated from one another, so that a sophisticated apparatus can be used on a patient for fracture reduction and then replaced, after reduction has been carried out by a simple fixation device, the reduction apparatus thus being freed for use on another patient. In particular, U.K. Pat. No. 2095999 provides a fracture reduction apparatus comprising means for holding the ends of bone fixation pins, and means for rotating the said holding means about three orthogonal axes passing through a point which is, in use, located at the site of the fracture and for moving the said holding means parallel to the said axes.

The apparatus described in U.K. Pat. No. 2095999 is capable of providing excellent results. However, it is complicated and, therefore, expensive, and it would therefore be desirable to have an apparatus which was capable of providing broadly comparable results but using a simpler and less expensive construction.

Attention is also drawn to United Kingdom Patent Specification No. 2110094A which describes a fracture reduction apparatus which includes two units each of which provides for rotation of a set of bone fixation pins about two orthogonal axes passing through the bone. The specification also refers to the possibility, though no details are given, of rotating the units about a rod, the axis of which is spaced from the bone. In contradistinction to this, as will be apparent from what is said below, each set of fixation pins used in the present invention is rotatable about three axes which all intersect one another at a point located in the bone.

BRIEF SUMMARY OF THE INVENTION

According to the present invention there is provided a fracture reduction apparatus comprising first holding means for holding first bone fixation means, second holding means for holding second bone fixation means, the first and second bone fixation means being located, in use, with the site of the fracture intermediate them, and means for rotating each of the said holding means about a respective set of three orthogonal axes, the three axes of each set intersecting one another at a respective point located in the bone, the two respective points being spaced from one another along the longitudinal axis of the bone.

DETAILED DESCRIPTION OF PREFERRED EMBODIMENT

Figure 1:
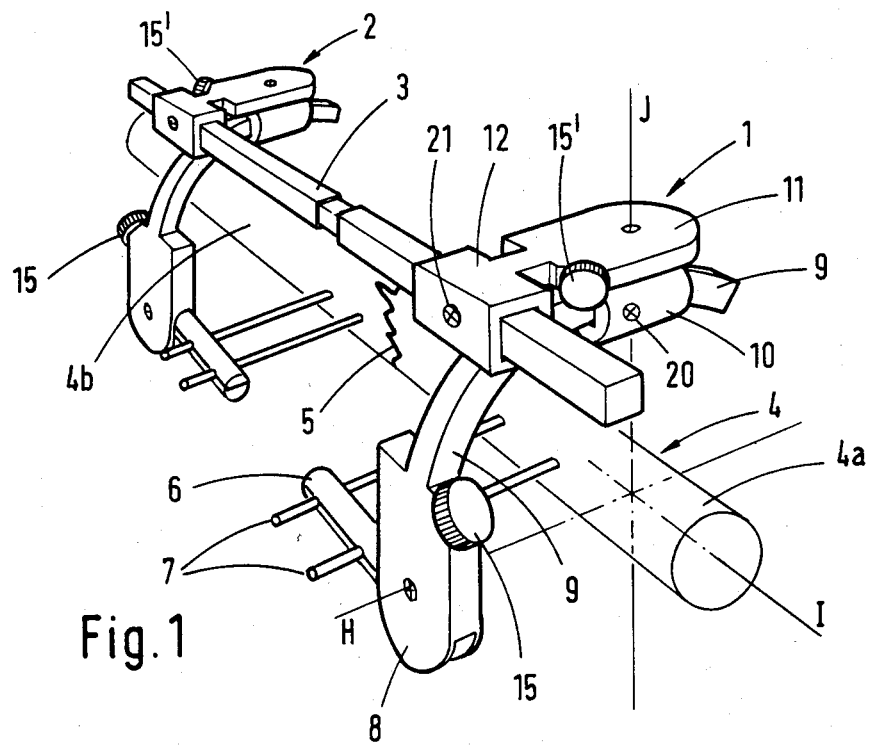
FIG. 1 is a perspective view showing a fracture reduction apparatus according to the invention in use.

As shown in FIG. 1, the apparatus comprises a pair of units 1 and 2 interconnected by a telescopic bar 3. The apparatus is shown in use in relation to a bone 4 having a fracture 5 which divides the bone 4 into segments 4a and 4b. The units 1 and 2 are mirror images of one another, and therefore only unit 1 will be described in detail below.

The unit 1 comprises a pin holder 6 which releasably clamps a pair of fixation pins 7. The pin holder 6 is mounted in a rotation unit 8 for pivotal movement with respect thereto about an axis H. As described further below with reference to FIG. 3A, the pin holder 6 and the rotation unit 8 are lockable in a predetermined orientation with respect to one another. The axis H is perpendicular to the longitudinal axis I of the bone segment 4a and passes through the bone.

The rotation unit 8 is fixedly connected to one end of a curved member 9. The member 9 passes through a unit 10 and is slidable therein. A locking means, for example a grub screw 20 is provided to selectively allow this movement or prevent it. Alternatively, the locking means may be similar to that shown for another purpose in FIG. 3A. The centre of curvature of the member 9 coincides approximately with the axis I. Thus, sliding movement of the member 9 with respect to the unit 10 causes the bone segment 4a to rotate approximately about the axis I.

A unit 11 is mounted on top of the unit 10 in such a way that the unit 10 is rotatable with respect to the unit 11 about an axis J. A locking means (described below in more detail with reference to FIG. 3B) is provided to permit this rotation or prevent it. The axis of rotation J is perpendicular to the axis I and, until there has been movement of the unit 8 about the axis I, perpendicular also to the axis H. The axis J passes through the bone, and it can be seen that the axes H, I and J intersect one another within the bone at what is substantially a point.

The unit 11 carries a rectangular cross-section tubular portion 12 within which the bar 3 is slidable. A locking means, for example a grub screw 21, is provided to allow or prevent this sliding movement.

Figure 3A:
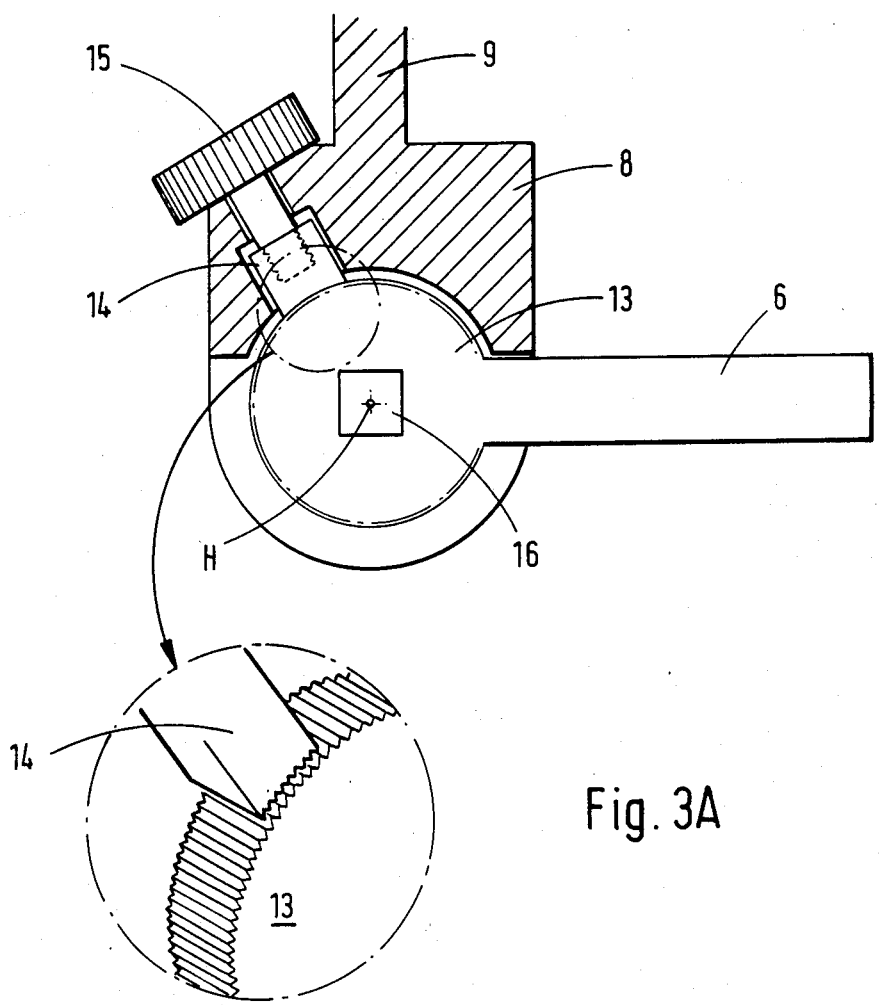
FIGS. 3A and 3B are sectional views showing details, on a larger scale, of the apparatus of FIG. 1.

FIG. 3A shows the locking means for locking or preventing movement of the pin holder 6 with respect to the rotation unit 8 about axis H. FIG. 3A is a vertical section through rotation unit 8 taken on a plane perpendicular to axis H. As can be seen from FIG. 3A, the proximal end of the pin holder 6 carries a wheel 13 having a serrated circumferential surface part of which is shown in the detailed view of FIG. 3A. A block 14 of rectangular cross-section and having a serrated lower face is mounted for radial movement with respect to the wheel 13. The block 14 is moved towards or away from the wheel 13 by means of an adjusting knob 15 which is in screw-threaded connection with the block 14. It should also be mentioned that the wheel 13 has a square central aperture 16 which, in use, receives a handle for a purpose described below.

Figure 3B:
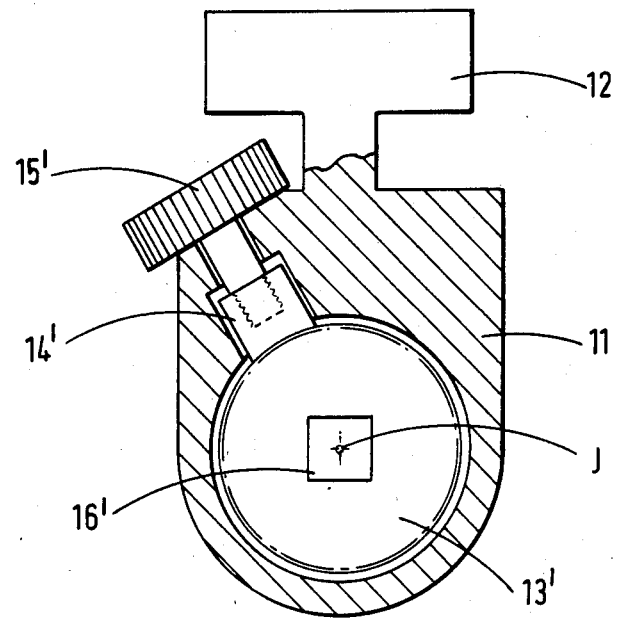

FIG. 3B shows a locking arrangement similar to that of FIG. 3A which is used to permit or prevent rotational movement of the unit 10 with respect to the unit 11 about the axis J. In FIG. 3B certain elements are denoted by reference numerals 13', 14', 15' and 16' which correspond to elements 13, 14, 15 and 16 in FIG. 3A, and no further detailed description of these elements is considered to be necessary. The unit 10 is connected to the wheel 13' on the opposite side thereof to that which is visible in FIG. 3B, by means of a short shaft which engages in the unit 10 and in the aperture 16'.

Figure 2A:
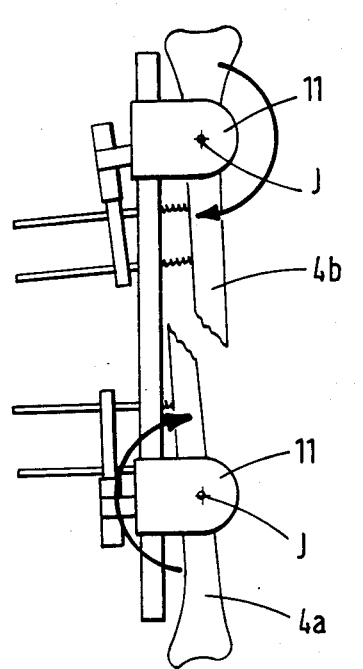
FIGS. 2A and 2B are diagrammatic plan views showing two modes of operation of the apparatus.
Figure 2B:
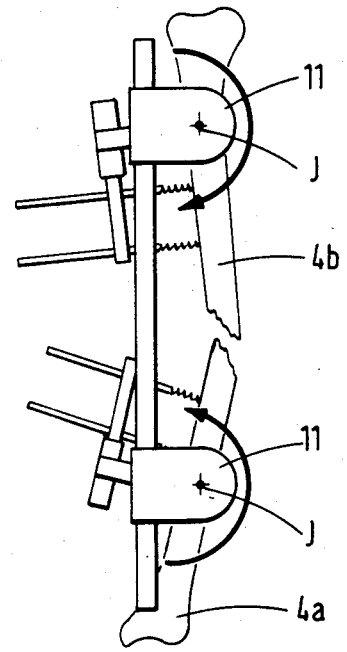

In use, the fixation pins 7 are inserted into the bone on either side of the fracture, as illustrated in FIG. 1. The distal ends of the pins 7 are clamped in the pin holder 6 of the unit 1 and the corresponding pin holder of the unit 2. To enable this to be done the units 1 and 2 must be an appropriate distance apart, and this is achieved by permitting sliding movement of the bar 3 with respect to the tubular portions 12. Reduction of the fracture is then carried out by combinations of the various movements which the reduction apparatus permits. The fracture may be distracted by lengthening the bar 3. This is done taking advantage of the telescopic nature of the bar, the two components of the bar in fact being interconnected by means of a screw thread. This is used rather than slidable movement of the bar 3 with respect to the tubular members 12 since it provides for better control and the possibility of carrying out the distraction under power. Axial rotation of the bone segments with respect to one another about the axis I is achieved by unlocking either of the units 10 and moving the curved bar 9 through it. Adjustments in the plane perpendicular to the axis J are carried out by combining rotations of the two units 11 about the respective axes J. Rotating them in the same direction corrects linear displacement (see FIG. 2A) whilst rotating them in opposite directions corrects angular displacement (see FIG. 2B). The same procedure is carried out in the orthogonal plane, perpendicular to axis H, by rotating the rotation units 8 about the respective axes H with respect to the pin holders 6.

This rotation is achieved by inserting a handle (not shown) into the aperture 16 by FIG. 3A.

It will be noticed that neither the units 1 and 2 nor the bar 3 significantly impede X-ray observation of the fracture site. This means that the fracture site can be continuously viewed during reduction by means of a low intensity X-ray apparatus. It is also important to notice that each of the axes of rotation is dealt with separately in the reduction process. Thus, the operator of the fracture reduction apparatus knows that once the bone segments are correctly aligned as far as one of these axes of rotation is concerned subsequent rotation about other axes will not affect the correctness of the first adjustment. This is particularly important when one bears in mind that the X-ray apparatus produces a two-dimensional image. If, as is the case with most conventional forms of fracture reduction apparatus, an initially correct adjustment about one axis is disturbed by effecting adjustment about a subsequent axis, much time can be spent in moving back and forth between various adjustment axes trying to get all the axes simultaneously correct.

Figure 4:
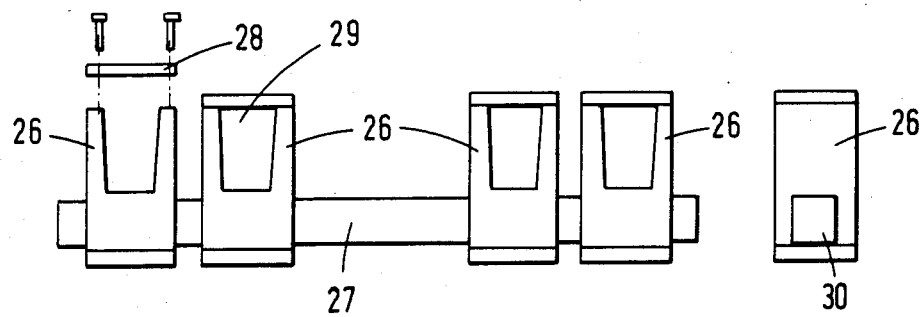
FIG. 4 shows a fixator for use with the apparatus of FIGS. 1 to 3.

When the best possible reduction has been achieved an external fixator is applied to the bone fixation pins and the fracture reduction apparatus is removed for subsequent use with another patient. FIG. 4 shows a preferred form of fixator. This comprises four or more identical blocks 26 which can be rigidly held at any location on a square-section rod 27. Each block has a removal cap 28 which, when in place, defines an aperture 29 in the block. In use, each fixation pin passes through the aperture in one of the blocks which is then filled with bone cement. In FIG. 4 an additional block 26 is shown at the right hand side thereof, rotated through 90° to show the aperture 30 in which the rod 27 is received.

I claim:

1. A fracture reduction apparatus comprising first holding means for holding first bone fixation means, second holding means for holding second bone fixation means, the first and second bone fixation means being located, in use, with the site of the fracture intermediate them, and means for rotating each of the said holding means about a respective set of three orthogonal axes, the three axes of each set intersecting one another at a respective point located in the bone, the two respective points being spaced from one another along the longitudinal axis of the bone.

2. An apparatus according to claim 1, wherein a first unit comprises the first holding means, a second unit comprises the second holding means, and the first and second units are mounted on a connecting member which spaces the units apart about the longitudinal axis of the bone.

3. An apparatus according to claim 2, wherein at least one of the first and second units is mounted for movement with respect to the connecting member, whereby to vary the distance by which the units are spaced apart.

4. An apparatus according to claim 2, wherein the connecting member comprises a first portion on which the first unit is mounted, a second portion on which the second unit is mounted, said first and second portions being telescopically interconnected whereby to vary the distance by which the units are spaced apart.

5. An apparatus according to claim 2, wherein each unit comprises first mounting means in which the respective holding means is rotatably mounted for rotation about an axis perpendicular to the longitudinal axis of the bone, second mounting means which receives a portion of the first mounting means to permit arcuate movement of the first mounting means about the longitudinal axis of the bone, and third mounting means on which the second mounting means is rotatably mounted to permit rotation of the second mounting means with respect to the third mounting means about an axis perpendicular to the axis of rotation of the holding means and to the longitudinal axis of the bone, the third mounting means being itself mounted on said connecting member.

6. An apparatus according to claim 5, comprising first locking means for selectively preventing or permitting rotation of the holding means with respect to the first mounting means, second locking means for selectively preventing or permitting said arcuate movement of the first mounting means, and third locking means for selectively preventing or permitting rotation of the second mounting means with respect to the third mounting means.

* * * * *